United States Patent
Aaltonen et al.

(10) Patent No.: US 10,080,374 B2
(45) Date of Patent: Sep. 25, 2018

(54) CHEESE AND PREPARING THE SAME

(75) Inventors: Terhi Aaltonen, Helsinki (FI); Päivi Myllärinen, Helsinki (FI); Ilkka Huumonen, Lapinlahti (FI); Emmi Martikainen, Espoo (FI)

(73) Assignee: VALIO LTD., Helsinki (FI)

( * ) Notice: Subject to any disclaimer, the term of this patent is extended or adjusted under 35 U.S.C. 154(b) by 0 days.

(21) Appl. No.: 14/126,540

(22) PCT Filed: Jun. 14, 2012

(86) PCT No.: PCT/FI2012/050604
§ 371 (c)(1),
(2), (4) Date: Jan. 29, 2014

(87) PCT Pub. No.: WO2012/172179
PCT Pub. Date: Dec. 20, 2012

(65) Prior Publication Data
US 2014/0220178 A1    Aug. 7, 2014

(30) Foreign Application Priority Data
Jun. 16, 2011  (FI) .................................... 20115607

(51) Int. Cl.
A23C 9/12      (2006.01)
A23C 19/00     (2006.01)
(Continued)

(52) U.S. Cl.
CPC ........ A23C 19/068 (2013.01); A23C 19/0328 (2013.01); A23C 19/05 (2013.01);
(Continued)

(58) Field of Classification Search
CPC ... A23C 19/0328; A23C 19/05; A23C 19/068; A23C 2210/202; A23C 2210/252; C12Y 203/02013
(Continued)

(56) References Cited

U.S. PATENT DOCUMENTS 7,585,537 B2    9/2009 Merrill et al.
2003/0054069 A1    3/2003 Han et al.
(Continued)

FOREIGN PATENT DOCUMENTS

CN    1256886 C    5/2006
CN    101420861 A    4/2009
(Continued)

OTHER PUBLICATIONS

TG.A.H. De Jong, G. Wijngaards, and S.J. Koppelman Transglutaminase Inhibitor from Milk. Journal of Food Science—vol. 68, Nr. 3, 2003; 820-825.*
(Continued)

*Primary Examiner* — Subbalakshmi Prakash
(74) *Attorney, Agent, or Firm* — Nixon & Vanderhye P.C.

(57) ABSTRACT

The present invention relates to a process for producing cheese, comprising the steps of: providing a first raw material liquid; providing a second raw material liquid; treating the first raw material liquid with a protein crosslinking enzyme to provide an enzyme-treated raw material liquid; mixing the enzyme-treated raw material liquid with the second raw material liquid to provide cheese milk; processing the cheese milk into cheese. The process produces cheese in improved yields while retaining the organoleptic properties of cheese unchanged. The invention further relates to cheese treated with a protein crosslinking enzyme, having the moisture on a fat-free basis of 67% or less and a protein profile of cheese has proteins of molecular weight of less than 66 kDa.

25 Claims, 2 Drawing Sheets

(51) Int. Cl.
    *A23C 19/068*    (2006.01)
    *A23C 19/032*    (2006.01)
    *A23C 19/05*     (2006.01)

(52) U.S. Cl.
    CPC   *C12Y 203/02013* (2013.01); *A23C 2210/202* (2013.01); *A23C 2210/252* (2013.01)

(58) Field of Classification Search
    USPC .................................... 426/10, 36, 40, 582
    See application file for complete search history.

(56) References Cited

U.S. PATENT DOCUMENTS

| | | | |
|---|---|---|---|
| 2005/0031603 A1* | 2/2005 | Hubertus de Jong | A23C 9/1425 424/94.1 |
| 2005/0123645 A1 | 6/2005 | Kumazawa et al. | |
| 2009/0068312 A1 | 3/2009 | Sasaki et al. | |

FOREIGN PATENT DOCUMENTS

| | | |
|---|---|---|
| EP | 0 711 504 | 5/1996 |
| EP | 0 726 317 | 8/1996 |
| EP | 0 966 887 | 12/1999 |
| EP | 1 048 218 | 11/2000 |
| EP | 1 057 411 | 12/2000 |
| EP | 1 057 412 | 12/2000 |
| EP | 1 197 152 | 4/2002 |
| EP | 1 201 136 A1 | 5/2002 |
| EP | 1 232 692 | 8/2002 |
| EP | 1 254 601 | 11/2002 |
| EP | 1 442 663 | 8/2004 |
| EP | 1 946 656 | 7/2008 |
| EP | 2 011 402 | 1/2009 |
| EP | 2 052 626 | 4/2009 |
| EP | 2 332 421 | 6/2011 |
| JP | H08-173032 | 7/1996 |
| JP | 9-131180 | 5/1997 |
| JP | 11-508448 | 7/1999 |
| JP | 2002-369653 | 12/2002 |
| JP | 2003-134997 | 5/2003 |
| JP | 2004-512344 | 4/2004 |
| JP | 2007-501611 | 1/2007 |
| JP | 2008-017814 | 1/2008 |
| KR | 10-0813107 B1 | 3/2008 |
| WO | WO 97/01961 | 1/1997 |
| WO | WO 02/35942 | 5/2002 |
| WO | WO 03/075668 | 9/2003 |
| WO | WO 2005/013710 | 2/2005 |
| WO | WO 2007/123223 | 11/2007 |
| WO | WO 2008/017499 | 2/2008 |
| WO | WO 2010/035825 | 4/2010 |

OTHER PUBLICATIONS

M.P. Bönisch, S. Lauber, and U. Kulozik. Cross-linking of heat-treated casein by transglutaminase Journal of Food Science—vol. 69, Nr. 8, 2004.*

Caiqiong Zhou, et al., "Food Nutrition", China Higher Education Press, p. 253, May 2011.

Burghagen, "Food Chemistry", China Agricultural University Press, p. 419, Feb. 2008.

Benheng Gu, et al., "Modern Dairy Products Processing", p. 504, China Light Industry Press, Jun. 2001.

Office Action issued in corresponding CN App. No. 201280029694.0 (dated Dec. 24, 2014) (with partial English Translation).

Bonisch et al., "Influence of transglutaminase protein cross-linking on the rennet coagulation of casein", *Food Hydrocolloids*, 2007, vol. 22, No. 2, pp. 288-297.

Volken de Souza et al., "Enzymatic properties of transglutaminase produced by a new strain of Bacillus circulans BL32 and its action over food proteins", *LWT Food Science and Technology*, vol. 44, No. 2, Mar. 1, 2011, pp. 443-450.

International Search Report for PCT/FI2012/050604, dated Jul. 17, 2012.

FI Search Report for 20115607, dated Feb. 7, 2012.

Chinese Office Action in Application No. 201280029694.0 dated Sep. 14, 2015 (with partial translation).

Japanese Office Action in Application No. 2014-515240 dated Mar. 29, 2016 (w/partial translation).

Russian Office Action in Application No. 2013157826/10 (090092) dated May 26, 2016 (w/ partial translation).

* cited by examiner

CHEESE AND PREPARING THE SAME

This application is the U.S. national phase of International Application No. PCT/FI2012/050604 filed 14 Jun. 2012 which designated the U.S. and claims priority to FI Patent Application No. 20115607 filed 16 Jun. 2011, the entire contents of each of which are hereby incorporated by reference.

FIELD OF THE INVENTION

The present invention relates to cheese making, and more particularly to a process for producing cheese using a protein crosslinking enzyme.

BACKGROUND OF THE INVENTION

Generally, there are several methods for milk clotting/gelation, in particular acidification and renneting. Besides, also an enzymatic, covalent crosslinking can induce a gelation of proteins. Therefore several possible applications of transglutaminase in milk products are given. However, an incubation of transglutaminase in milk or milk concentrates even at high enzyme concentrations does not result in a gelation due to the electrostatic repulsion between the casein micelles at neutral pH-values. Therefore, transglutaminase alone is not a sufficient reagent for the preparation of a relatively firm cheese. Only by a reduction of this electrostatic repulsion through a pH-drop or through the effect of rennet at relevant protein concentrations and relevant transglutaminase concentrations a gelation may be achieved.

Amino acids of animal- and plant-based proteins may be crosslinked by enzymes, such as transglutaminase (EC 2.3.2.13) in a known manner. Covalent bonds formed in the enzyme treatment withstand different process conditions, such as heating and mixing, well. From milk proteins, caseins and particularly the κ-casein, are the best substrate for transglutaminase. The β-casein also contains a lot of glutamine and lysine, which are joined together by a transglutaminase enzyme.

In cheese making, transglutaminase is used to increase the cheese yield, with optional approach to coprecipitate whey proteins with casein. In milk, transglutaminase in particular crosslinks casein proteins whereby a network structure is formed, which results in increased yields of a cheese curd. It has been found that heat treatment of milk still enhances the protein crosslinking activity of transglutaminase.

It is known that milk contains substances that inhibit the activity of transglutaminase. These inhibiting substances are deactivated in a heat treatment of milk. On the other hand, it is known that the content of said substances in relation to the total content of proteins and fat is reduced in ultrafiltration of milk.

EP 1057411 A2 discloses a process for incorporating whey proteins into cheese using transglutaminase. Transglutaminase treatment is executed on liquid which is fortified with whey protein. A further liquid containing casein is blended with the transglutaminase-treated liquid. A rennet is then added to provide a cheese curd with a high proportion of whey proteins.

EP 0711504 A1 discloses a process for producing cheese using transglutaminase. Transglutaminase is added to a milk protein solution before, after or simultaneously with the addition of a milk clotting enzyme. It is reported that a cheese curd is produced in a larger amount compared to the conventional methods.

WO 97/01961 discloses a process for making cheese where transglutaminase is added to cheesemilk and incubated for a suitable period. A rennet is then added to provide a coagulate which is further processed into cheese. It is reported that improved yields of cheese are obtained.

Drawback of the above cheese making processes using transglutaminase is that there are processes where transglutaminase remains active, whereby deficiencies in organoleptic properties are arised in resulting cheese products, especially during ripening and a long-term storage. Organoleptic failures such as defects in taste, aroma and texture can be seen in ripened cheese in particular. Also, problems in subsequent coagulation of cheese milk with a rennet can be foreseen in the known cheese making processes.

As stated above, it is known that a cheese yield can be increased by using transglutaminase in cheese making. In particular, transglutaminase increases the amount of caseinomacropeptides in cheese. However, if transglutaminase is added in too large amounts to cheese milk, the subsequent coagulation of the cheese milk with a rennet is inhibited. Moreover, it has been found that transglutaminase remains active during ripening of cheese which makes the ripened cheese tough. Thus, it is highly important that the addition of transglutaminase to cheese milk and the incubation time with transglutaminase are carefully controlled in order to provide cheeses in an efficient manner without reduction of organoleptic properties of the resulting cheese.

BRIEF DESCRIPTION OF THE INVENTION

It has now been found a process for producing cheese where cheese with good organoleptic properties is obtained in improved yields by the use of a protein crosslinking enzyme.

In an aspect, the invention provides a process for producing cheese, comprising the steps of:
  providing a first raw material liquid containing casein,
  providing a second raw material liquid,
  treating the first raw material liquid with a protein crosslinking enzyme to provide an enzyme-treated raw material liquid,
  mixing the enzyme-treated raw material liquid with the second raw material liquid to provide cheese milk,
  processing the cheese milk into cheese using a coagulant.

It was surprisingly found that cheese can be produced in increased yields by treating only a portion of cheese milk with a protein crosslinking enzyme while the process technical problems in cheese production, and deficiencies in organoleptic properties of cheese caused by the enzyme are avoided. Without wishing to be bound to any theory, it is believed that the improved yield is a result of the formation of a crosslinked network and retention of caseinomacropeptides in cheese matrix, wherefore water is bound in increased amounts in cheese. Despite an increased amount of bound water no changes in organoleptic characteristics or softening of cheese can be observed.

The invention provides is a cost-effective process for producing cheese where consumption of the raw materials can be reduced due to the increased amount of bound water without impairing the organoleptic properties of cheese. It is known that cheese yield can be increased by whey proteins. However, whey proteins have an unfavourable effect on the organoleptic properties, especially taste, of cheese.

To avoid well known problems in coagulation, and the further excessive crosslinking of the protein during ripening of cheese, the enzyme is allowed to act for a suitable period of time, and then deactivated by adding a solution containing substances that inhibits the activity of the enzyme. It is an essential character of the present invention that the enzyme is deactivated before an actual cheese making process. Since only a portion of the cheese milk is treated with the enzyme, reduced amounts of the enzyme compared to those conventionally spent in cheese making can be used to still achieve improved yields of cheese.

Moreover, the protein crosslinking enzyme has a beneficial effect on preservability of cheese, since the cheese is not softened but the texture is remained.

The invention provides an economical, efficient and simple process for production of cheese.

The process of the invention can be used for preparing semi-soft, semi-hard, hard and extra-hard ripened and unripened cheeses, as well as processed cheeses. The process is also suitable for cheese-like products, where milk fat and/or protein is replaced by another suitable fat or protein, or both, partly or completely.

In another aspect, the invention provides cheese treated with a protein crosslinking enzyme, having the moisture on a fat-free basis of 67% or less and a protein profile with proteins of molecular weight less than 66 kDa.

DETAILED DESCRIPTION OF THE INVENTION

Figure 1:
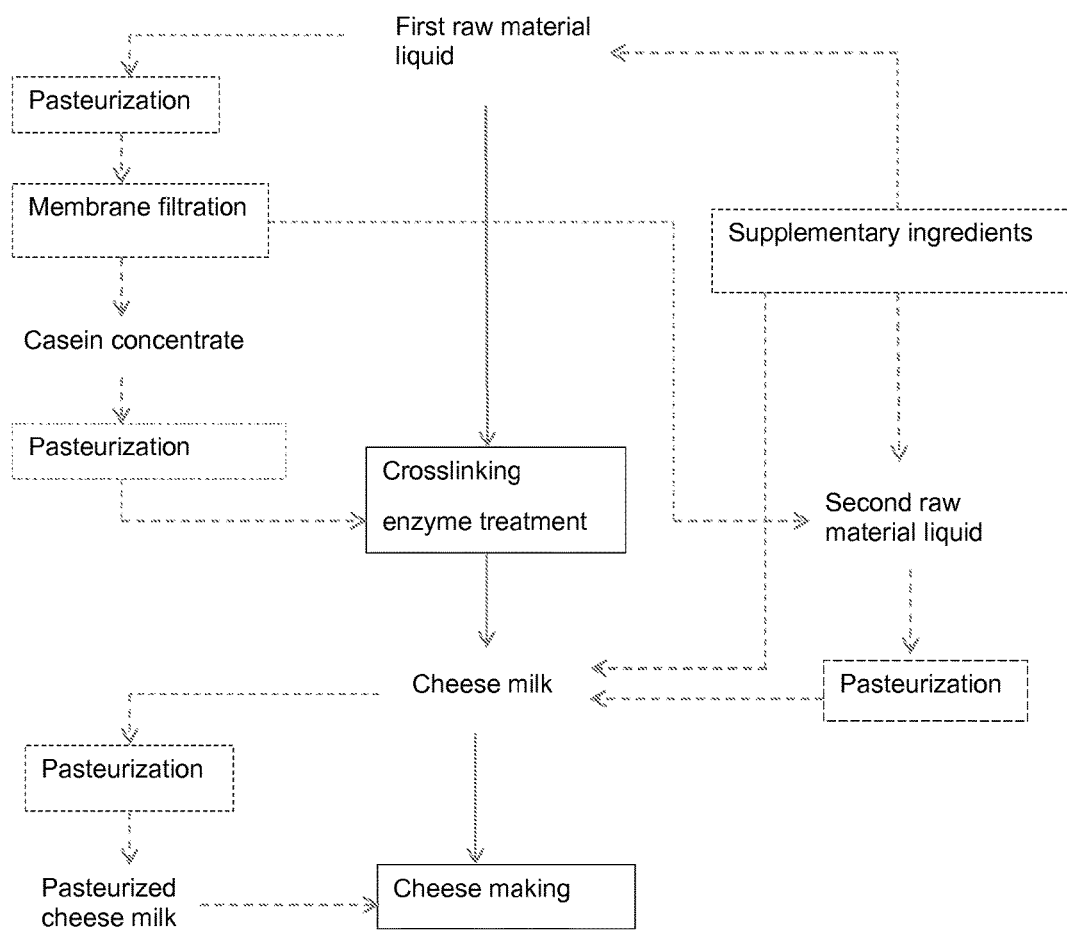
FIG. 1 is a flow chart showing some embodiments of the process of the invention.

In an aspect, the invention provides a process for producing cheese, comprising the steps of:
providing a first raw material liquid containing casein,
providing a second raw material liquid,
treating the first raw material liquid with a protein crosslinking enzyme to provide an enzyme-treated raw material liquid,
mixing the enzyme-treated raw material liquid with the second raw material liquid to provide cheese milk,
processing the cheese milk into cheese using a coagulant.

The invention provides a process for producing cheese in improved yields.

In the present invention,
the term "cheese milk" means the milk material used for cheese making;
the term "cheese" also means cheese-like products. In a cheese-like product, milk fat and/or protein is replaced by another suitable fat or protein, or both, partly or completely. Another suitable protein is derived from plants, such as soybean. Typically, milk fat is partly replaced by edible fat, typically of plant origin, such as rapeseed oil, fractionated palm oil or coconut oil. Also, lard can be used;
the term "raw material liquid" may be milk as such obtained from an animal, such as a cow, sheep, goat, camel, mare or any other animal that produces milk suitable for human consumption, or milk that is preprocessed as desired. The raw material liquid may thus be, for instance, full-fat (whole) milk, cream, low fat milk, skim milk, buttermilk, vegetable oils, rinsing waters (washing waters) derived from streams obtained from washing/rinsing of processing pipes, containers and vessels in dairy and plant (vegetable) product manufacturing plants, colostrum, low-lactose milk, lactose-free milk, whey protein depleted milk, reconstituted (recombined) milk from milk powder, organic milk, or a combination of any of these as such or as a concentrate or pre-treated as a desired manner, such as heat-treated.

The raw material liquid may be supplemented with ingredients generally used in the preparation of milk products, such as fat, protein, ash (minerals) or sugar fractions, or the like.

Among the various suitable raw material liquids listed above, the first raw material liquid is selected from those containing casein. The first raw material liquid is not fortified with whey protein. In an embodiment, the first raw material includes at most 5% of whey protein. In another embodiment, the first raw material includes at most 2% of whey protein. In an embodiment, the first raw material liquid is skim milk.

The second raw material is selected from those containing substances that inhibit the activity of the protein crosslinking enzyme. In an embodiment, the second raw material liquid includes skim milk, cream or a mixture thereof. In still another embodiment, the second raw material liquid may be membrane filtrated first raw material liquid, i.e. a fraction containing substances that inhibit the activity of the protein crosslinking enzyme originating from the first raw material liquid. Typically, such second raw material liquids include permeates of ultrafiltrated first raw material liquid, diafiltrated first raw material liquid, microfiltrated first raw material liquid, or mixtures thereof. The permeate(s) can also be originated from separate processes for preparing milk products. The permeate itself can be used as a second raw material, or it can be combined with any other suitable second raw material liquid.

The protein of the first raw material liquid is modified with a crosslinking enzyme. The protein crosslinking enzyme suitable for use in the process of the invention may be any enzyme that is known to crosslink milk protein. These enzymes include transglutaminase, laccase, tyrosinase, peroxidase, sulfhydryl oxidase, glucose oxidase, protein-glutaminase, etc. Said enzymes can be used alone or in any combinations with each other.

In an embodiment of the invention, the enzyme is transglutaminase (EC 2.3.2.13). It is commonly known that transglutaminase crosslinks amino acids of animal and vegetable proteins. Of milk proteins, caseins and κ-casein in particular are the best substrates for transglutaminase. β-casein, too, is rich in glutamine and lysine that the enzyme links together.

Transglutaminase can be any transglutaminase commonly used in dairy industry. It can be derived from a microbial source, fungus, mould, fish and a mammal. In an embodiment of the invention, transglutaminase is isolated from a microbial source.

There are several commercially available transglutaminase enzyme preparations that are suitable for use in the process of the invention. These include Activa®YG (Ajinomoto, Japan), Activa®MP (Ajinomoto, Japan), and Yiming-TG (Yiming Fine Chemicals Co., Ltd., China). Optimum conditions depend on the enzyme used and they can be obtained from the manufacturers of the commercial enzymes.

Tyrosinases (EC 1.14.18.1) can be derived from variety of plant, animal and fungal species, i.e. filamentous fungus *Trichoderma reesei*. It is commonly known that laccase (EC 1.10.3.2) from fungi and bacteria (*Trametes hirsuta*) hetero-crosslinks carbohydrates and proteins.

The amount of the protein crosslinking enzyme added to the first raw material liquid ranges from 0.2 to 10 U/g protein. In an embodiment, the amount is 1 to 5 U/g protein.

Some embodiments of the process of the invention, including several optional steps, are illustrated in FIG. 1. The optional steps are indicated with a dash line.

The first raw material liquid can be directly subjected to a treatment with a protein crosslinking enzyme without any pre-treatment. In an embodiment, prior to the enzyme treatment, the first milk raw material is subjected to a heat treatment. It has been found that crosslinking between the milk proteins of the heat treated raw material liquid by means of the enzyme is taken place to a great extent. Even polymerization of the proteins can be seen. Heat treatment thus further enhances the effect of the protein crosslinking enzyme.

Examples of heat treatments to be used are pasteurization, high pasteurization, or heating at a temperature lower than the pasteurization temperature for a sufficiently long time. Specifically, UHT treatment (e.g. milk at 138° C., 2 to 4 s), ESL treatment (e.g. milk at 130° C., 1 to 2 s), pasteurization (e.g. milk at 72° C., 15 s), or high pasteurization (at least 85° C., at least 4 s, e.g. milk at 95° C., 5 min) can be mentioned. The heat treatment can be either direct (vapor to milk, milk to vapor) or indirect (tube heat exchanger, plate heat exchanger, scraped-surface heat exchanger).

In an embodiment, the first raw material liquid is subjected to a membrane filtration in order to concentrate casein protein for further treatment with a protein crosslinking enzyme. In the membrane filtration, substances inhibiting the activity of said enzyme are passed into a permeate while casein protein is concentrated in the retentate. The membrane filtration is preferably carried out, since the inhibiting substances are removed and transglutaminase can act actively. Thus, a larger proportion of the milk proteins can be treated with the same amount of the enzyme resulting in increased yields of cheese.

In an embodiment, the first raw material liquid is subjected to heat treatment as described for the first raw material liquid prior to membrane filtration.

In an embodiment, a portion of the permeate obtained from the membrane filtration of the first raw material liquid is used as a second raw material liquid or as a portion of it.

Suitable membrane filtrations for use in the present invention are ultrafiltration and microfiltration, optionally performed with a diafiltration technique. In an embodiment of the invention, membrane filtration is ultrafiltration. The concentration factor of ultrafiltration is typically in the range of 1 to 10. In an embodiment, the concentration coefficient is 2 to 5.

The casein content of the casein concentrate obtained from the membrane filtration is about 2.7 to 35% by weight. In an embodiment, the casein content is about 12% by weight. The whey protein content of the casein concentrate is at most 5%. In an embodiment, the whey protein content is at most 2%.

The casein concentrate may be heat-treated as described for the first raw material liquid.

The first raw material liquid, optionally heated, or preferably a membrane filtrated casein concentrate of the first raw material liquid, optionally heated, is treated with a protein crosslinking enzyme to provide an enzyme-treated raw material liquid. Generally, the treatment is continued for about 15 minutes to 24 hours at a temperature ranging from about 4° C. to 40° C. In an embodiment, the treatment is carried out at 15° C. for 3 hours. The enzyme treatment is carried out in a manner commonly known in the art.

Typically, about 5% to 50% by weight of the proteins of the cheese milk is treated with a protein crosslinking enzyme. In an embodiment, about 20% of the proteins of the cheese milk are treated.

The enzyme-treated raw material liquid is mixed with a second raw material liquid to provide cheese milk. In this process step, the protein crosslinking enzyme is deactivated in order to avoid any problems in subsequent process steps for producing cheese, and any adverse effects on the organoleptic properties of the resulting cheese. The second raw material liquid can be any raw material liquid that contains substances inhibiting the activity of the protein crosslinking enzyme. In an embodiment, the second raw material liquid includes skim milk, cream or a mixture thereof.

The second raw material liquid is added to the first raw material liquid in an amount sufficient to deactivate the protein crosslinking enzyme in the first raw material liquid. In an embodiment, the added amount of the second raw material liquid is 50% to 95% by volume of the cheese milk. The protein content of the cheese milk is about 3.2% to 4.5% by weight.

A portion of the second raw material may be heat-treated as described for the first raw material liquid. In an embodiment, at most 25% by volume of the second raw material liquid is high pasteurized. In an embodiment, high pasteurization is performed at a temperature of at least 85° C. for at least 4 seconds. In still another embodiment, at most 25% by volume of the second raw material is high pasteurized at 95° C. for 20 seconds.

The cheese milk formed from the first raw material liquid treated with a protein crosslinking enzyme, and the second raw material liquid containing substances inhibiting the activity of the enzyme can be supplemented with other ingredients, like various natural components of milk such as milk minerals, vitamins, additives, processing aids, etc. The supplementary ingredients can be a substance containing milk proteins, carbohydrates and/or fat. The supplementary ingredients can be derived, for example, from side streams obtained from processing of dairy products. Also, rinsing waters having a protein content up to 3% are suitable. If appropriate, the supplementary ingredients can be in powdered forms. The supplementary ingredients can also be vegetable fat, such as coconut fat, whereby cheese-like products are obtained. In an embodiment, the supplementary ingredient is butter milk substantially composed of water and carbohydrate with minor amounts of fat and proteins. The amount of the supplementary ingredients is typically up to 10% by weight of the cheese milk.

The supplementary ingredients can be introduced to the first raw material liquid, the second raw material liquid and/or to the cheese milk at one or more stages of the process of the invention.

In an embodiment of the process of the invention, skim milk is concentrated with ultrafiltration to provide a casein concentrate. The concentrate is then treated with transglutaminase (TG) to provide a TG-treated concentrate. In an embodiment, cheese milk is prepared from 6% to 8% by volume of the TG-treated concentrate, 2% to 12% by volume of cream, and 80% to 90% by volume of skim milk. The protein content of the cheese milk of about 4.2% by weight is achieved. The cheese milk can be processed to various cheese products in a conventional manner typical of each cheese type.

In another embodiment of the invention, cheese milk is prepared from 2% to 8% by volume of the TG-treated skim milk, 2% to 12% by volume of cream, and 85% to 96% by volume of skim milk. The protein content of the cheese milk of about 3.6% by weight is achieved. The cheese milk can be processed to various cheese products in a conventional manner typical of each cheese type.

In still another embodiment of the invention, cheese milk is prepared from 2% to 8% by volume of the TG-treated skim milk, 2% to 12% by volume of cream, 75% to 86% by volume of skim milk, and 5% to 10% by volume of butter milk. The protein content of the cheese milk of about 3.4% by weight is achieved. The cheese milk can be processed to various cheese products in a conventional manner typical of each cheese type.

The cheese milk can be pasteurized before it is further processed to cheese. Pasteurization can be performed, for example, at 73° C. for 15 seconds. Pasteurization of the cheese milk is advantageous, since it further deactivates transglutaminase.

The cheese milk, or the pasteurized cheese milk, is further processed to cheese in a manner generally known in the art. The process of the invention can be used for preparing semi-soft, semi-hard, hard and extra-hard ripened and unripened cheeses. The cheese prepared by the process of the invention can also be used as a raw material in the preparation of processed cheeses.

The expressions soft, semi-soft, semi-hard (solid), hard and extra hard are strictly defined in FAO/WHO A-6-1968 Codex General Standard for Cheese using their composition on the basis of the water content of the fat-free portion (MFFB %). Thus, soft cheese in the present application refers to cheese whose water content of the fat-free part is more than 67%, semi-soft cheese in the present application refers to cheese whose water content of the fat-free part is 61 to 69%, semi-hard cheese in the present application refers to cheese whose water content of the fat-free part is 54 to 63%, hard cheese in the present application refers to cheese whose water content of the fat-free part is 49 to 56%, and extra hard cheese in the present application refers to cheese whose water content of the fat-free part is less than 51%.

Various ingredients typically used for each cheese type are incorporated in cheese milk which is then processed to cheese. The ingredients and process techniques used for each cheese type are generally known to a person skilled in the art of cheese making. If desired, an acidifier like starter, acidogen, for example GDL, and a coagulant, like rennet, chymosin, lactic acid, citric acid, hydrochloric acid, oxalic acid and calcium salt, are included in the cheese milk. Different starters and starter mixtures may be used. The most common starters include a mesophilic starter (lactococcal starter), typically starters by Christian Hansen or Danisco, propionibacteria, typically Valio PJS, and a taste imparting adjunct (mesophilic and/or thermophilic adjunct starter), typically thermophilic Valio Lb 161 (shocked/non-shocked). For example, a mesophilic 0-starter, R-608 by Christian Hansen, is used as a starter. The starter and its amount depend on the cheese type and the conditions used. It is known that the amount of bulk starter is usually 0.5 to 2%, typically 0.7 to 0.8%. The amount of DVS starter (DVS/DVI) is usually 0.001 to 0.2%, typically 0.01 to 0.05%. In addition to a bulk starter, the method of the invention may use, for example, LH-32, BS-10 and CR-312 by Christian Hansen as such or in different combinations and amounts depending on the cheese and cheese-like product to be made as additional starters to impart taste. Alternatively, taste imparting adjunct starters may be added substantially simultaneously with other ingredients.

In the present invention, cheese milk is coagulated using a coagulant. Coagulation means simultaneous clotting and gel forming which are taken place by chemical or physical means. In the chemical coagulation, an acidifier or a ferment, such as a starter, an acid, an acidogen, for example GDL, lactic acid, citric acid, hydrochloric acid or oxalic acid are included. In the physical coagulation, coagulation is performed by means of a coagulant, such as rennet and chymosin, high pressure treatment of heating. In an embodiment of the invention, the coagulant comprises a starter, chymosin or both.

In another aspect, the invention provides cheese which is treated with a protein crosslinking enzyme, having the moisture on a fat-free basis of 67% or less and a protein profile with proteins of molecular weight of less than 66 kDa.

The following examples are present for further illustration of the invention without limiting the invention thereto.

EXAMPLES

Example 1

Skim milk was concentrated with ultrafiltration to a concentration factor of 3.3 and to a protein concentration of 12%. The concentrate was heated to 15° C., and 3 U/g, based on protein of the concentrate, of transglutaminase was added. The concentrate was incubated at 15° C. for 3 hours. After incubation cheese milk was standardized with 7% by volume of cream, 85% by volume of skim milk and 8% by volume of the concentrate to a protein content of 4.2% by weight and fat content 2.94% by weight. After standardization, cheese milk was pasteurized at 72° C. for 15 s.

Cheese milk was heated to 33° C. and 0.005% by weight of DVS-R608 (Hansen) and 0.002% by weight of CHN19 (Hansen) starter cultures were added. After 1 hour incubation, 0.08% by weight of $CaCl_2$ and 0.005% by weight of chymosin were added, and after 30 min incubation coagulated cheese milk was cut to small cubes and cheese curd was formed. Curd was cooked in a cheese vat for one hour. After mixing, whey was removed, and curd was moulded, pressed and brined. Cheese was ripened for 4 weeks at 12° C.

Cheese yield was calculated from four separate cheese vats. The results are shown in Table 1. It was observed that transglutaminase increased cheese yield significantly. Cheese composition before brining is shown Table 2. It was observed that the composition on the basis of the water content of the fat-free portion (MFFB %) was significant higher in cheese treated with transglutaminase (TG-cheese) than in control cheese having no transglutaminase treatment. However, textural measurement showed that hardness of the control cheese and that of TG cheese did not differ statistically (Table 3). Control cheese was prepared accordingly without crosslinking enzyme treatment.

TABLE 1

Cheese yield (%) and cheese milk to cheese (kg/kg) (mean value of 4 separate cheese vats).

|  | Cheese yield (%) | Cheese milk to cheese (kg/kg) |
|---|---|---|
| TG cheese (invention) | 13.30a | 7.5a |
| Control cheese | 12.58b | 7.9b |

TABLE 2

Cheese composition before ripening

|  | Fat (%) | Total solids (%) | MFFB (%) | Protein (%) |
|---|---|---|---|---|
| TG cheese (invention) | 23.1 | 51.1 | 63.6 | 24.5 |
| Control cheese | 24.1 | 53.1 | 61.8 | 25.5 |

TABLE 3

Cheese hardness results from textural measurement

|  | Hardness | |
|---|---|---|
|  | Mean (g) | SD |
| TG cheese (invention) | 24000a | 2000 |
| Control cheese | 24400a | 800 |

Figure 2:
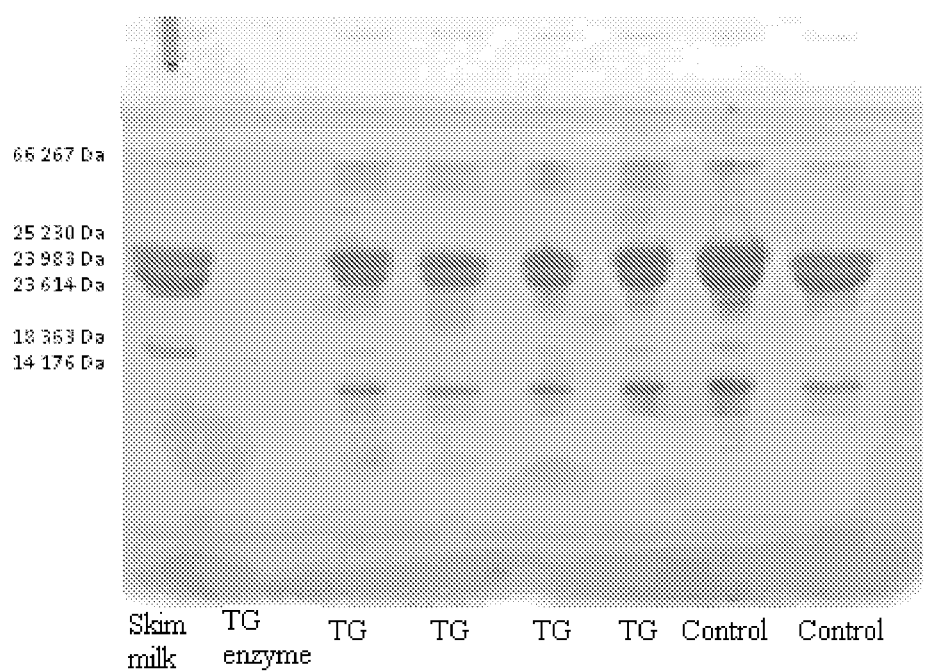
FIG. 2 is a SDS-page showing protein profiles of cheese treated with transglutaminase ("TG") and of control cheese with no transglutaminase treatment ("Control"). References are a transglutaminase solution ("TG enzyme") and skim milk.

Protein profiles (SDS-Page) of cheese according to invention and of control cheese are shown in FIG. 2. As references, protein profiles of TG-enzyme solution and skim milk are shown. Cheese according to invention has a protein profile with proteins of molecular weight less than 66 kDa. The SDS-page shows that transglutaminase crosslinks the milk proteins resulting in higher molecular weight proteins.

Example 2

Skim milk was heated to 40° C. and it was treated with 2 U/g, based on protein from skim milk, of transglutaminase and incubated for 15 min. After incubation, cheese milk was standardized with 5% by volume of the above skim milk treated with transglutaminase, 90% by volume of skim milk without transglutaminase treatment, and 5% by volume of cream. The resultant cheese milk was pasteurized at 73° C. for 15 s.

After cooling, cheese milk was heated to 33° C. and 0.005% by weight of DVS-R608 (Hansen) and 0.002% by weight of CHN19 (Hansen) starter cultures were added. After 1 hour incubation, 0.08% CaCl$_2$ and 0.005% chymosin were added and after 30 min incubation coagulated cheese milk was cut to small cubes and cheese curd was formed. Curd was cooked in a cheese vat for an hour. After mixing, whey was removed, and curd was moulded, pressed and brined. Cheese was ripened for 4 weeks at 12° C. Control cheese was prepared accordingly without crosslinking enzyme treatment.

Cheese yield is shown in table 4. It was observed that transglutaminase increased cheese yield statistically. Cheese composition before brining is shown table 5. It was observed that MFFB was significant higher in TG-cheese than in control cheese. However, textural differences were not observed.

TABLE 4

|  | Cheese yield | |
|---|---|---|
|  | Cheese yield (%) | Cheese milk to cheese (kg/kg) |
| TG cheese (invention) | 13.10a | 7.6 |
| Control cheese | 12.41b | 8.1 |

TABLE 5

Cheese composition before ripening

|  | Fat (%) | Total solids (%) | MFFB (%) | Protein (%) |
|---|---|---|---|---|
| TG cheese (invention) | 23 | 51.1 | 63.5 | 22.5 |
| Control cheese | 24.5 | 54.1 | 60.8 | 26.5 |

It will be obvious to a person skilled in the art that, as the technology advances, the inventive concept can be implemented in various ways. The invention and its embodiments are not limited to the examples described above but may vary within the scope of the claims.

The invention claimed is:

1. A process for producing cheese, comprising the steps of:
providing a first raw material liquid containing casein,
providing a second raw material liquid containing substances that inhibit the activity of a protein crosslinking enzyme,
treating the first raw material liquid with the protein crosslinking enzyme to provide an enzyme-treated raw material liquid,
mixing the enzyme-treated raw material liquid with the second raw material liquid to provide cheese milk, and
processing the cheese milk into cheese using a coagulant, wherein the proteins of the cheese have a molecular weight of less than 66 kDa.

2. The process of claim 1, wherein the protein crosslinking enzyme is transglutaminase, laccase, tyrosinase, peroxidase, sulfhydryl oxidase, glucose oxidase, protein-glutaminase, or a mixture thereof.

3. The process of claim 1, wherein the first raw material liquid is not fortified with whey protein.

4. The process of claim 1, wherein the whey protein content of the first raw material is at most 5%.

5. The process of claim 1, wherein the first raw material liquid is pasteurized.

6. The process of claim 1, wherein the cheese milk is pasteurized.

7. The process of claim 1, wherein the first raw material liquid is subjected to a membrane filtration to provide a casein concentrate which is treated with the protein crosslinking enzyme.

8. The process of claim 7, wherein the membrane filtration is ultrafiltration, microfiltration, ultrafiltration/diafiltration, or microfiltration/diafiltration.

9. The process of claim 7, wherein the casein concentrate is pasteurized.

10. The process of claim 7, wherein the protein content of the casein concentrate is about 2.7 to 35% by weight.

11. The process of claim 1, wherein about 5% to 50% by weight of the proteins of the cheese milk is treated with the protein crosslinking agent.

12. The process of claim 1, wherein the protein crosslinking enzyme is added in an amount of 0.2 to 10 U/g protein.

13. The process of claim 1, wherein the protein crosslinking enzyme is incubated with the first raw material liquid for a period between 15 minutes and 24 hours at a temperature ranging from 4° C. to 40° C.

14. The process of claim 1, wherein the second raw material liquid includes skim milk, cream or a mixture thereof.

15. The process of claim 1, wherein the second raw material liquid includes a permeate obtained from the membrane filtration of the first raw material liquid.

16. The process of claim 1, wherein at most 25% by volume of the second raw material liquid is high pasteurized.

17. The process of claim 1, wherein the protein content of cheese milk is about 3.2 to 4.5% by weight.

18. The process of claim 1, wherein the cheese milk is pasteurized at a temperature of 65° C. to 80° C. for 10 to 120 seconds before it is processed to cheese.

19. Cheese produced according to the method of claim 1, wherein the cheese has a moisture content on a fat-free basis of 67% or less, and wherein the proteins of the cheese have a molecular weight of less than 66 kDa.

20. The process of claim 2, wherein the protein cross-linking enzyme is transglutaminase.

21. The process of claim 4, wherein the whey protein content of the first raw material is at most 2%.

22. The process of claim 8, wherein the membrane filtration is ultrafiltration.

23. The process of claim 10, wherein the protein content of the casein concentrate is about 12% by weight.

24. The process of claim 11, wherein about 20% by weight of the proteins of the cheese milk is treated with the protein crosslinking agent.

25. The process of claim 12, wherein the protein cross-linking enzyme is added in an amount of 1 to 5 U/g protein.

* * * * *